US005314952A

United States Patent [19]

Choi et al.

[11] Patent Number: 5,314,952

[45] Date of Patent: May 24, 1994

[54] PROCESSES FOR PRODUCING HIGHLY WATER ABSORPTIVE RESINS

[75] Inventors: Su B. Choi; Huyng M. Lee; Myung J. Kim; Tae H. Jang, all of Daejeon, Rep. of Korea

[73] Assignee: Lucky, Ltd., Seoul, Rep. of Korea

[21] Appl. No.: 659,352

[22] PCT Filed: Jun. 8, 1990

[86] PCT No.: PCT/KR90/00005

§ 371 Date: Apr. 22, 1991

§ 102(e) Date: Apr. 22, 1991

[87] PCT Pub. No.: WO90/15829

PCT Pub. Date: Dec. 27, 1990

[30] Foreign Application Priority Data

| | | | |
|---|---|---|---|
| Jun. 21, 1989 | [KR] | Rep. of Korea | 89-8596 |
| Jun. 21, 1989 | [KR] | Rep. of Korea | 89-8597 |
| Jul. 3, 1989 | [KR] | Rep. of Korea | 89-9405 |
| Jul. 3, 1989 | [KR] | Rep. of Korea | 89-9406 |
| Jul. 27, 1989 | [KR] | Rep. of Korea | 89-10672 |
| Jul. 27, 1989 | [KR] | Rep. of Korea | 89-10673 |
| Oct. 7, 1989 | [KR] | Rep. of Korea | 89-14440 |

[51] Int. Cl.$^5$ .......................... C08F 2/32; C08F 8/00; C08F 8/14; C08F 20/06

[52] U.S. Cl. .................................... 525/119; 525/360; 525/366; 525/385; 526/73; 526/207; 526/241; 526/317.1

[58] Field of Search ................... 575/119, 385; 526/73

[56] References Cited

U.S. PATENT DOCUMENTS

| | | | |
|---|---|---|---|
| 4,340,706 | 7/1982 | Obayashi | 526/207 |
| 4,497,930 | 2/1985 | Yamasaki | 524/556 |
| 4,806,578 | 2/1989 | Kobayashi | 523/402 |

*Primary Examiner*—Fred Zitomer

*Attorney, Agent, or Firm*—Townsend and Townsend; Khourie and Crew

[57] ABSTRACT

The processes for producing highly water absorptive resins of the present invention comprise the following steps: (A) suspending an aqueous solution of partially neutralized alkali metal acrylate and optionally partially neutralized acrylamido alkane sulfonate in a hydrocarbon solvent containing a surfactant having a HLB value of $3 \approx 6$ or $8 \approx 12$; (B) subjecting the mixture to inverse suspension polymerization in the presence of at least one water soluble radical polymerization initiator; (C) if necessary, separating the moisture from the produced polymer by azeotropic distillation to reduce the water content to about 15 to 55% by weight; (D) adding a crosslinking agent having two or more reactive groups such as epoxy groups, if desired, as a solution form to subject the surface of the polymer to crosslinking reaction; and optionally (E) subjecting to coagulation with the use of a coagulant in the presence of an inert solvent, whereafter drying the resultant coagulate to obtain the water absorptive resin.

8 Claims, 1 Drawing Sheet

PROCESSES FOR PRODUCING HIGHLY WATER ABSORPTIVE RESINS

BACKGROUND OF THE INVENTION

1. Field of the Invention

The present invention relates to processes for producing highly water absorptive resins having excellent water absorbency and saline solution absorbency. More particularly, it relates to processes for producing highly water absorptive resins having a high water absorption rate and water absorptive capacity, and an excellent gel-strength.

2. Description of the Prior Art

Various water absorbing materials such as sponge, pulp, paper and the like, are well known in the art. Also various synthetic products made by graft polymerization of materials containing a hydrophilic group, such as —OH, —$NH_2$, —COOH, and the like, have been used conventionally. However, such water absorbing materials, e.g. a sponge, a pulp, and a paper, are characterized with physical mechanisms for absorbing water so that such materials have defects in that the majority of the absorbed water can be easily squeezed out by the application of external pressure. In recent years, in order to solve these defects, synthetic water-absorptive products having particular physical and chemical characteristics have been developed. The majority of such synthetic products are crosslinked polyacrylic acid salts, polymethacrylic acid salts, crosslinked polyacrylic acid-methacrylic acid copolymer salts, crosslinked saponification products of starch-acrylonitrile graft copolymer, and cellulose and acrylate-grafted copolymer. Such grafted products are on the market as sanitary napkins, sanitary pads, and diapers in the sanitary field, water absorbing containers in the civil and gardening field, and anti-dewdrop agents in the construction field.

However, although saponificated products of starch-acrylonitrile graft copolymer have a relatively high deionized water-absorbency, the saline-solution thereof is poor. Also, long-term storage is impossible due to the main component being starch.

On the other hand, partially crosslinked polyacrylic acid salts have high water absorption rates and capacity in saline solution as well as in deionized water, and they can be stored for a long period of time. Particularly, commercially available alkali metal acrylates are used as a starting material to prepare a water absorptive resin in the present invention.

Various processes are known for polymerizing acrylic acid and alkali acrylate, including bulk polymerization, aqueous solution polymerization, spray polymerization, inverse emulsion polymerization, inverse suspension polymerization, and the like. With the exception of inverse emulsion polymerization and inverse suspension polymerization, it is difficult to remove the heat of polymerization, and the viscosity of the polymerization mixture becomes too high to carry out general polymer production. Moreover, according to these processes it is difficult to obtain particulate polymers.

An example of the inverse emulsion polymerization process is disclosed in U.S. Pat. No. 3,284,393. When, for example, acrylic acid is used as the starting material, the obtained polymer is insoluble in water and does not have such an absorbency that the polymer can be called a water absorptive resin even if it is neutralized with an alkali such as sodium hydroxide or the like.

As a process for producing an acrylic acid-alkali metal acrylate polymer having a water absorbency, the inverse suspension polymerization process is mentioned in Japanese Patent Publication No. 79-30710. According to this process, a water absorptive polymer is prepared through a stable reaction by the use of a sorbitan fatty acid ester having a HLB (Hydrophilic-Lipophilic Balance) value of $3\sim6$. The resin thus obtained has a high deionized water absorbency corresponding to $400\sim500$ times its own weight; however, the saline solution-absorbency of said water absorptive resin is as low as $35\sim50$ times its own weight.

In U.S. Pat. No. 4,497,930, there is disclosed a method for producing a water absorbent polymer comprising the steps of subjecting acrylic acid and sodium acrylate to polymerization in the presence of a sorbitan fatty acid ester having a HLB value of $3\sim6$ as a dispersing agent, and adding a crosslinking agent with stirring in methanol to crosslink the surface of the resulting polymer. However, a disadvantage is that the water absorptive resin prepared by this method is unsatisfactory in water absorptive capacity because the polymerization reaction is carried out at temperatures too low (70°-75° C.) to stabilize the reaction.

In general, a highly water absorptive resin requires good water absorption rate, water absorptive capacity and gel-strength. These characteristics exhibit mutually opposing correlations with each other; therefore, some characteristics are partially sacrificed in order to improve other characteristics.

The foregoing three properties, namely the water absorptive capacity, the water absorption rate and the gel-strength in the water absorbent resin, are influenced by many factors such as a polymer particle's size and shape, the kinds of crosslinking agent and dispersing agent used, CMC (Critical Micelle Concentration), polymerization temperature, and so on.

In the inverse emulsion polymerization and the inverse suspension polymerization W/O systems, it is known that the use of a surfactant having a HLB value of $3\sim6$ produces a stable system. But according to these polymerization reactions, the resultant particles are too minute and have many hydrophobic groups in their surface, such that the particulate polymer is swollen too slowly when contacted with water. Consequently, the water absorption rate and the water absorptive capacity become deteriorated. To solve the foregoing problem, a surfactant having a HLB value of $8\sim12$, which is known to be unstable in the inverse emulsion and suspension polymerization systems, may be used. However, another problem, reaction control, arises due to agglomeration.

On the other hand, U.S. Pat. No. 4,340,706 discloses a water absorbent resin suitable for usages which require stability in the fluid-absorbed state for long periods of time. However, even the resin obtained by this method is insufficient in its rate of water absorption due to a lack of surface-crosslinking. Furthermore, in cases where the resin is prepared at low temperatures (55°$\sim$60° C.) using this method, undesired residual monomers are obtained in large quantities.

Representative methods for improving the water absorption rate include increasing the surface area of the resin (i.e. decreasing the apparent specific gravity), crosslinking the surface of the particulate polymer after polymerization, or adding inorganic materials. Among the foregoing methods, the method of adding inorganic materials such as silica is advantageous. The dispersing rate of particulate polymer is remarkably improved and agglomeration of polymer particles is prevented. However, there is a disadvantage in that it is difficult to obtain the desired water absorption rate due to a poor sedimentation rate of the particulate polymer. When using the method of crosslinking the surface of the particulate polymer to improve the water absorption rate, there are also disadvantages. Minute particles which are formed tend to blow off and to agglomerate together, making it difficult to obtain a satisfactory water absorption rate.

SUMMARY OF THE INVENTION

The present invention resides in highly water absorptive resins and methods for their production. Water absorptive resins having excellent water absorption properties can be obtained by carrying out the characteristic processes comprising the following steps:

(a) suspending an aqueous solution of partially neutralized alkali metal acrylate, wherein about 50 to 100% of the carboxyl groups have been neutralized to their alkali metal salts and optionally acrylamido alkane sulfonate wherein about 50 to 100% of the sulfonic groups have been neutralized to their alkali metal salts, in a hydrocarbon solvent containing a surfactant having a HLB value of 3~6 or 8~12;

(b) subjecting the mixture to inverse suspension polymerization in the presence of at least one water soluble radical polymerization initiator;

(c) if necessary, separating the moisture from the produced polymer by azeotropic distillation to reduce the water content to about 15 to 55% by weight;

(d) adding a crosslinking agent having two or more reactive groups such as epoxy groups, if desired, as a solution, preferably in methanol, to subject the surface of the polymer to a crosslinking reaction; and optionally (e) coagulating the polymer of step (d) with a coagulant in the presence of an inert solvent and drying the resultant coagulate to obtain the water absorptive resin.

An object of the present invention is to provide improved processes for preparing highly water absorptive resins having excellent water absorption properties.

BRIEF DESCRIPTION OF THE INVENTION

In order to better understand the invention reference will be made to the accompanying drawing in which:

FIG. 1 is a microphotograph (×200) of the water absorptive resin having irregular shape according to Example 27; and FIG. 2 is a microphotograph (×200) of the spherical water absorptive resin according to Comparative Example 26.

DETAILED DESCRIPTION OF THE INVENTION

Figure 1:

According to the present invention, there are provided highly water absorptive resins and processes for preparing them.

In the present invention, the polymers used include, for example, polyacrylic acid, polymethacrylic acid, or a copolymer thereof with maleic acid, acrylamide, 2-acrylamido-2-methylpropylsulfonic acid, 2-methacryloylethane sulfonic acid, 2-hydroxyethyl methacrylate, or the like in a certain proportion. The most preferred polymer is polyacrylic acid.

The first preferred embodiment of the invention is a process for preparing a highly water absorptive resin, which comprises the following steps;

(a) suspending an aqueous solution of partially neutralized alkali metal acrylate wherein about 50 to 100% by mole of the carboxyl groups have been neutralized to their alkali metal salts and at least one water soluble radical polymerization initiator, in a hydrocarbon solvent containing a surfactant having a HLB value 8~12;

(b) subjecting the mixture to inverse suspension polymerization at temperatures of 75° to 95° C.;

(c) separating the moisture from the produced polymer by azeotropic distillation to reduce the water content to about 35 to 55% by weight, and removing the solvent by filtration to obtain a particulate polymer;

(d) adding a crosslinking agent that has three or more reactive epoxy groups, that is dissolved in methanol, wherein the amount of the crosslinking agent is 0.5~2.5% by weight based on the polymer, and that conducts surface-crosslinking for 1-2 hours at temperatures of 70° to 85° C.; and (e) washing the polymer of step (d) with methanol, filtering, and drying at temperatures of 90° to 175° C.

The alkali metal acrylate can be obtained by neutralizing acrylic acid with an alkali metal hydroxide such as lithium hydroxide, sodium hydroxide, potassium hydroxide and calcium hydroxide. The degree of neutralization is preferably about 50~100% by mole, more preferably about 65~80% by mole. When the degree of neutralization is lower than about 50% by mole, the hydroxide concentration is decreased resulting in an electronic density in the water which is also small such that the penetration intensity is decreased. Thus the desired highly water absorptive resin would not be obtained. The concentration of the monomer thus produced, i.e., the alkali metal acrylate and the unneutralized acrylic acid, is about 20~70% by weight based on the total weight of the composition and the preferred monomer concentration is about 40~60% by weight.

Any surfactant having a HLB value of 8~12 and containing many hydrophilic groups may be used in this invention. Preferred are sorbitan monolaurate (SPAN 20, manufactured by ICI Americas Inc., HLB value=8.6) and Ryoto Sugar Ester S-970® (manufactured by Mitsubishi-Kasei Food Corporation (MFC), HLB value=9). Particularly preferred is Ryoto Sugar Ester S-970®.

In general, if a surfactant having a HLB value of 8~12, and having more hydrophilic groups than hydrophobic groups, is used in the polymerization of the water absorptive resin, the possibility of contact with the hydrophilic monomer of the starting material is increased. As a result, the inverse emulsion polymerization system and the inverse suspension polymerization system become very unstable, resulting in increased viscosity of the suspension due to the Trommsdorff effect and a reaction which is very rapidly progressed. Consequently, it causes both the agglomeration of particulate polymer due to the Weigenberg effect and a rapidly emitted heat of polymerization.

However, according to the present invention these disadvantages can be prevented resulting in a stable polymerization system. In addition, it is unnecessary to separately add a crosslinking agent during polymerization. A self-crosslinking reaction and a pseudocrosslinking reaction take place to improve greatly the absorbency of the polymer obtained. Also, the surface of the polymer thus obtained is crosslinked with the use of a crosslinking agent having three or more reactive groups such as epoxy groups in the presence of an inert solvent such as methanol, such that the polymer absorbs the methanol containing the crosslinking agent and becomes swollen. This allows the crosslinking agent to permeate easily into the surface of the particulate polymer for the surface-crosslinking reaction to take place. As a result, the water absorption rate and gel-strength of the resin become remarkably improved.

The water soluble radical polymerization initiators used in this invention are well known in the art of polymer chemistry, for example, ammonium persulfate, potassium persulfate, hydrogen peroxide, and the like. The preferred water soluble radical polymerization initiator is potassium persulfate. The above-mentioned polymerization initiator may be used alone or in admixtures of two or more.

The hydrocarbon solvent used in the present invention is an aliphatic or aromatic hydrocarbon, which has a boiling point of 30°~200° C. Examples thereof are n-hexane, n-heptane, cyclohexane, and the like. The preferred solvent is cyclohexane.

The surface-crosslinking agent used is one having at least three or more reactive groups such as epoxy groups, for example, glycerol polyglycidyl ether, trimethylol propane polyglycidyl ether and sorbitol polyglycidyl ether, preferably glycerol polyglycidyl ether. In crosslinking step (d), methanol is preferred as an inert solvent for improving the surface-crosslinking effect.

The process for preparation of the highly water absorptive resin according to the first preferred embodiment of the present invention is described in detail as follows:

(1) Preparation of the partially neutralized alkali metal acrylate

A reactor, equipped with a condenser, a dropping funnel and a stirrer, is charged with acrylic acid. An alkali metal hydroxide is dissolved in water in a beaker separately to form an alkali metal hydroxide solution. The alkali metal hydroxide solution is fed dropwise to the reactor through the dropping funnel while being kept at less than 30° C. This neutralizes 50~100% by mole of the acrylic acid to produce an equivalent amount of an alkali metal acrylate having the degree of neutralization of 50~100% by mole. When the neutralization step is conducted at a temperature of over 45° C., one of the reactants could be polymerized.

(2) Inverse suspension polymerization step

A reactor with a condenser having a Dean-Stark trap, a pressure-equalizing dropping funnel and a stirrer is charged with a surfactant and a hydrocarbon solvent, and then the temperature is raised to 75~95° C. A mixture of the partially neutralized alkali metal acrylate prepared in step (1) and a water-soluble radical polymerization initiator is fed to the reactor in small portions and polymerized completely for about 1 hour.

(3) Azeotropic distilling step

The resultant polymer contains a large amount of water so that it is difficult for the crosslinking agent to react with the surface of the polymer. The moisture contained in the polymer is separated by azeotropic distillation to reduce the water content of the polymer to about 35 to 55% by weight. When the water content is less than 35% by weight, it is uneconomic. On the other hand, when the water content is over 55% by weight, the effect of surface-crosslinking is decreased. After separating the water from the polymer, the temperature of the reactor is cooled to room temperature. The solvent is removed by filtration.

(4) Surface-crosslinking step

The polymer produced in step (3) is crosslinked by the crosslinking agent so as to improve water absorption rate and gel-strength. The polymer and the crosslinking agent are dissolved in methanol and added to a reactor equipped with a condenser, a stirrer, and a dropping funnel. The temperature is held between 75° and 80° C., and the surface-crosslinking reaction is carried out for 1 to 2 hours. The polymer thus treated is cooled to room temperature and the methanol is removed by filtration.

(5) Washing and drying step

To remove residual monomers, the obtained polymer is washed twice with methanol and filtered. The filtered polymer is dried at a temperature of 90° to 175° C. and passed through a 50-mesh wire gauze to obtain the water absorptive resin having a uniform size. The water absorption rate and water absorptive capacity of the obtained resin are measured by the filtering method.

The second preferred embodiment of the invention is a process for preparing a highly water absorptive resin, which comprises the following steps:

(a) suspending an aqueous solution of partially neutralized alkali metal acrylate wherein about 50 to 100% by mole of the carboxyl groups have been neutralized to their alkali metal salts and at least one water soluble radical polymerization initiator, in a hydrocarbon solvent containing a surfactant having a HLB value of 8~12;

(b) subjecting the mixture to inverse suspension polymerization at temperatures of 55° to 60° C.;

(c) separating the moisture from the produced polymer by azeotropic distillation to reduce the water content to about 15 to 45% by weight;

(d) adding a crosslinking agent having three or more reactive epoxy groups, and which is dissolved in methanol (10~30% by weight based on the polymer), and subjecting the mixture to surface-crosslinking for 1 to 2 hours at temperatures of 70° to 85° C.;

(e) cooling down to room temperature and then filtering to obtain the surface-crosslinked polymer; and (f) subjecting to coagulation with the use of a coagulant dissolved in methanol of 3~5 times by weight based on the polymer, wherein the amount of the coagulant is 0.5~3.0% by weight based on the polymer, whereafter the resultant coagulate is dried.

The alkali metal acrylate, the surfactant, the water soluble radical polymerization initiator, the hydrocarbon solvent and the surface-crosslinking agent are the same as described in the foregoing first preferred embodiment of this invention.

The coagulant is a proton-releasing acid such as sulfuric acid, acetic acid, nitric acid, or hydrochloric acid. The preferred coagulant is sulfuric acid.

The process for preparation of the highly water absorptive resin according to the second preferred embodiment of the present invention is described in detail as follows:

(1) Preparation of the partially neutralized alkali metal acrylate

A reactor equipped with a condenser, a dropping funnel and a stirrer is charged with acrylic acid. An alkali metal hydroxide is dissolved in water in a beaker separately to form an alkali metal hydroxide solution. The alkali metal hydroxide solution is fed dropwise to the reactor through the dropping funnel while being kept at less than 30° C. and neutralizing 50~100% by mole of the acrylic acid to produce an equivalent amount of an alkali metal acrylate having the degree of neutralization of 50~100% by mole. When the neutralization step is conducted at a temperature of over 45° C., one of the reactants could be polymerized.

(2) Inverse suspension polymerization step

A reactor, equipped with a condenser having a Dean-Stark trap, a pressure-equalizing dropping funnel and a stirrer, is charged with a surfactant and a hydrocarbon solvent, and then the temperature is raised to 55°~60° C. A mixture of the partially neutralized alkali metal acrylate prepared in step (1) and a water soluble radical polymerization initiator is fed to the reactor in small portions, and polymerized completely for about 3 hours.

(3) Azeotropic distilling and surface-crosslinking step

The moisture contained in the resultant polymer is separated by azeotropic distillation to reduce the water content of the polymer to about 15 to 45% by weight. When the water content is less than 15% by weight, it is uneconomic. On the other hand, when the water content is over 45% by weight, the effect of surface-crosslinking is decreased.

After separating the water from the polymer, the solution of the crosslinking agent dissolved in methanol (methanol being 10~30% by weight, based on the polymer), is added, and the surface-crosslinking reaction is carried out for 1 hour. The amount of the crosslinking agent is 0.1~2.0% by weight. The reactor is maintained at room temperature, and then the solvent is removed by filtration to obtain the polymer.

(4) Coagulating step

After 0.5~3.0% by weight of sulfuric acid as a coagulant is dissolved in 3~5 times by weight, based on the polymer, of methanol, the polymer obtained in step (3) is added thereto and stirred at room temperature. The solvent is removed by filtration to collect the coagulate.

(5) Drying step

The resultant coagulate is dried at 120° C. for 1 hour and passed through a 40-mesh wire gauze to obtain the water absorptive resin. The water absorption rate of the obtained resin is measured by the filtering method.

The third preferred embodiment of this invention is a process for preparing a highly water absorptive resin, which comprises the following steps:

(a) suspending an aqueous solution of partially neutralized alkali metal acrylate wherein about 50 to 100% by mole of the carboxyl groups have been neutralized to their alkali metal salts, and at least one water soluble radical polymerization initiator, in a hydrocarbon solvent containing a surfactant having a HLB value of 3~6;

(b) subjecting the mixture to inverse suspension polymerization;

(c) separating the moisture from the produced polymer by azeotropic distillation to reduce the water content to about 15 to 50% by weight;

(d) adding a crosslinking agent having three or more reactive epoxy groups in an amount of 0.01~5% by weight based on the polymer, to subject the polymer of step (c) to surface-crosslinking; and (e) subjecting the surface-crosslinked polymer to coagulation with the use of a coagulant in the presence of an inert solvent, wherein the amount of the coagulant is 0.01~5% by weight based on the polymer.

The alkali metal acrylate and the water soluble radical polymerization initiator are the same as described in the foregoing first preferred embodiment.

As the surfactant, there may be used any surfactant having a HLB value of 3~6, and includes, for example, sorbitan fatty acid esters such as sorbitan monostearate, and sorbitan monolaurate, and cellulose esters such as ethyl cellulose, benzyl cellulose, ethylhydroxy cellulose, cellulose acetate, cellulose butyrate and cellulose acetate butyrate. Particularly preferred are the sorbitan fatty acid esters. The surfactant is preferably used in an amount of 0.5~15% by weight based on the monomer used.

As the hydrocarbon solvent used in the inverse suspension polymerization, there may be used an aliphatic or aromatic hydrocarbon having a boiling point of 30°~3200° C., which includes n-hexane, n-heptane, cyclohexane, and the like. The preferred solvent is n-hexane. The above-mentioned solvents may be used alone or in admixture of two or more. The solvent is used in an amount of preferably 0.1~50 parts by weight, more preferably 0.5~30 parts by weight, based on 1 part by weight of the monomer used.

The moisture-separating process may be carried out during or after polymerization. A water content of the polymer which is 20~50% (by weight based on the polymer), is advantageous in the surface-crosslinking reaction. On the other hand, when the water content is out of that range, the water absorptive capacity and the water absorption rate are lowered to an undesirable level.

The surface-crosslinking agent used in this invention is water soluble, and has at least three or more reactive groups such as epoxy groups which can react with the carboxyl or carboxylate moiety in a molecule. As the crosslinking agent, there may be used polyglycidyl ethers, chloroepoxy compounds, polyaldehydes, or the like. The amount of the surface-crosslinking agent is generally 0.01~5% by weight based on the polymer. When the amount is less than 0.01% by weight, the effect of the surface-crosslinking agent is insignificant. On the other hand, if the amount of the surface-crosslinking agent is over 5% by weight, the crosslinking density is increased such that the water absorptive capacity of the surface-crosslinked polymer is decreased.

Examples of the inert solvent used in the coagulation step (e) include lower alcohols such as methanol, ethanol, n-propyl alcohol, isopropyl alcohol, n-butyl alcohol, isobutyl alcohol, t-butyl alcohol or octyl alcohol, or a polyol such as ethylene glycol, propylene glycol, glycerin or diethylene glycol. The preferred inert solvent is methanol. The amount thereof is 50~500% by weight, preferably 100~300% by weight based on the polymer.

As the coagulant, there may be used a proton-releasing acid, for example, sulfuric acid, acetic acid, nitric acid, hydrochloric acid, and the like. The preferred coagulant is sulfuric acid. The amount of coagulant to be used depends on the kind of coagulant and the solvent used, and is generally 0.01~3% by weight based on the inert solvent used.

The fourth preferred embodiment of this invention is a process for preparing a highly water absorptive resin, which comprises the following steps:

(a) suspending an aqueous solution of partially neutralized alkali metal acrylate wherein about 50 to 100% by mole of the carboxyl groups have been neutralized to their alkali metal salts and at least one water soluble radical polymerization initiator, in a hydrocarbon solvent containing a surfactant having a HLB value of 3~6;

(b) subjecting the mixture to inverse suspension polymerization;

(c) adding a crosslinking agent having two or more reactive groups in an amount which is 0.01~5% by weight based on the polymer, to subject the mixture of step (b) to surface-crosslinking; and (d) subjecting the surface-crosslinked polymer to coagulation using a coagulant in the presence of an inert solvent, wherein the amount of the coagulant is 0.01~3% by weight based on the solvent.

The alkali metal acrylate, the surfactant, the hydrocarbon solvent, the water soluble radical polymerization initiator, the coagulant and the inert solvent used in the coagulation are the same as described in the foregoing third preferred embodiment.

The surface-crosslinking agent uses reactive groups such as epoxy groups which can react with the carboxyl or carboxylate groups in a molecule. Examples of the crosslinking agent are polyglycidyl ethers such as glycerol diglycidyl ether; chloroepoxy compounds such as epichlorohydrin and α-methylchlorohydrin; polyaldehydes such as glyoxal and glutaraldehyde; polyols such as glycerol and ethylene glycol; polyamines such as ethylenediamine, and the like. The preferred crosslinking agents are polyglycidyl ethers. The preferred amount is the same as described in the foregoing third preferred embodiment.

The fifth preferred embodiment of this invention is a process for preparing a highly water absorptive resin, which comprises the following steps:

(a) suspending an aqueous solution of partially neutralized alkali metal acrylate wherein about 50 to 100% by mole of the carboxyl groups have been neutralized to their alkali metal salts, and partially neutralized acrylamido alkane sulfonate (1~5% by weight, wherein about 50 to 100% by mole of the sulfonic groups have been neutralized to their alkali metal salts), and at least one water soluble radical polymerization initiator, in a hydrocarbon solvent containing a surfactant having a HLB value of 8~12;

(b) subjecting the mixture to inverse suspension polymerization at temperatures of 40° to 80° C.;

(c) separating the moisture from the produced polymer by azeotropic distillation to reduce the water content to about 15 to 45% by weight;

(d) adding a crosslinking agent, having three or more epoxy groups, dissolved in methanol, wherein the amount of the crosslinking agent is 0.1~2.0% by weight based on the polymer, to subject the polymer of step (c) to surface-crosslinking for 1 hour; and (e) subjecting the product of step (d) to coagulation using a coagulant in the presence of an inert solvent, and subsequently drying the resultant coagulate to obtain the water absorptive resin.

The alkali metal acrylate, the hydrocarbon solvent, the water soluble radical polymerization initiator, the surface-crosslinking agent, the coagulant and the inert solvent are the same as described in the foregoing first preferred embodiment, except that the amount of the crosslinking agent is preferably 0.1~2% by weight based on the polymer.

According to this invention, the 50~100% by mole-neutralized acrylamido alkane sulfonate which is represented by the following formula $$CH_2{=}CH\overset{O}{\overset{\|}{C}}NHCZ_2(CH_2)_nSO_3Y$$

(wherein Z is H or $CH_3$; n is an integer of 0 to 2; and Y is Na, K or Li) is used to improve the water absorption rate.

The process for preparation of the highly water absorptive resin according to the fifth preferred embodiment of the present invention is described in detail as follows:

(1) Preparation of the partially neutralized alkali metal acrylate

A reactor equipped with a condenser, a dropping funnel and a stirrer is charged with acrylic acid. An alkali metal hydroxide is dissolved in water in a beaker to form an alkali metal hydroxide solution. The alkali metal hydroxide solution is fed dropwise into the reactor through the dropping funnel while the temperature of the mixture is kept below 30° C. Approximately 50~100% by mole of the acrylic acid is neutralized to produce an equivalent amount of an alkali metal acrylate having the degree of neutralization of 50~100% by mole. When the neutralization step is conducted at a temperature of over 45° C., one of the reactants could be polymerized.

(2) Inverse suspension polymerization step

A reactor, equipped with a condenser having a Dean-Stark trap, a dropping funnel, a stirrer and a nitrogen gas inlet pipe, is charged with a surfactant and a hydrocarbon solvent and the temperature is raised to 40°~80° C. A mixture of the partially neutralized alkali metal acrylate prepared in step (1), a partially neutralized alkali metal acrylamido sulfonate, and a water soluble radical polymerization initiator is fed to the reactor in small portions and the resulting mixture is polymerized completely.

(3) Azeotropic distilling and surface-crosslinking step

The moisture contained in the polymer of step (2) is separated by azeotropic distillation to reduce the water content of the polymer to 15~45% by weight.

After separating the water from the polymer, a solution of the crosslinking agent dissolved in methanol is added and the surface-crosslinking reaction is carried out for 1 hour. The amount of the crosslinking agent is preferably 0.1~2.0% by weight based on the polymer.

(4) Coagulating and drying step

The polymer obtained by filtration, after the crosslinking reaction, is suspended in methanol, and sulfuric acid is added, to coagulate the polymer. The coagulate is collected by filtration and dried to obtain the water absorptive resin. The water absorption rate of the obtained resin is measured by the filtering method using an 80-mesh wire gauze.

The sixth preferred embodiment of the invention is a process for preparing a highly water absorptive resin, which comprises the following steps:

(a) suspending an aqueous solution of partially neutralized alkali metal acrylate wherein about 50 to 100% by mole of the carboxyl groups have been neutralized to their alkali metal salts, partially neutralized acrylamido alkane sulfonate (about 1~5% by weight, wherein about 50 to 100% by mole of the sulfonic groups have been neutralized to their alkali metal salts), and at least one water soluble radical polymerization initiator, in a hydrocarbon solvent containing a surfactant having a HLB value of 3~6;

(b) subjecting the mixture to inverse suspension polymerization at temperatures of 40° to 80° C.;

(c) separating the moisture from the produced polymer by azeotropic distillation to reduce the water content of the polymer to about 15 to 45% by weight;

(d) adding a crosslinking agent that has three or more reactive epoxy groups and that is dissolved in methanol (wherein the amount of the crosslinking agent is 0.1~2.0% by weight based on the polymer), to subject the produced polymer of step (c) to surface-crosslinking for 1 hour; and (e) coagulating the product of step (d) using a coagulant in the presence of an inert solvent, and subsequently drying the resultant coagulate to obtain the water absorptive resin.

The alkali metal acrylate, the hydrocarbon solvent, the surfactant solvent, the water soluble radical polymerization initiator, the coagulant and the inert solvent are the same as described in the foregoing third preferred embodiment. Additionally, the acrylamido alkane sulfonate is the same as described in the foregoing fifth preferred embodiment.

The surface-crosslinking agent may be one that has three or more reactive epoxy groups; for example, glycerol polyglycidyl ether, trimethylol propane polyglycidyl ether or sorbitol polyglycidyl ether. The amount of the crosslinking agent is 0.1~2% by weight based on the polymer.

Water absorptive resin according to the sixth preferred embodiment is the same as described in the foregoing fifth preferred embodiment.

The seventh preferred embodiment of the invention is a process for preparing a highly water absorptive resin, which comprises the following steps:

(a) suspending an aqueous solution of partially neutralized alkali metal acrylate (wherein about 50 to 100% by neutralized alkali metal acrylate (wherein about 50 to 100% by mole of the carboxyl groups have been neutralized to their alkali metal salts) and at least one water soluble radical polymerization initiator, in a hydrocarbon solvent containing a surfactant having a HLB value of 8~12;

(b) subjecting the mixture to inverse suspension polymerization while raising the internal temperature of the reactor successively to 70° C., to 60°~67° C., to 70° C., and then to 75° C., to undergo phase-transition;

(c) during or after the polymerization, separating the moisture from the produced polymer by azeotropic distillation to reduce the water content to about 15 to 55% by weight, and then filtering to remove the solvent;

(d) adding a crosslinking agent that has three or more reactive epoxy groups and that is dissolved in methanol, wherein the amount of the crosslinking agent is 0.005~15% by weight based on the produced polymer, to subject the product of step (c) to surface-crosslinking for 1 to 2 hours at temperatures of 70° to 85° C.; and (e) washing the product of step (d) with methanol, filtering, and drying at temperatures of 90° to 175° C. to obtain the water absorptive resin.

The present inventors have found a surprising fact that irregularly shaped, highly water absorptive resins can be obtained by carrying out polymerization in the presence of a surfactant having a HLB value of 8~12 while raising the reaction temperature successively to 70° C., to 60°~67° C., to 70° C. and to 75° C., to undergo phase-transition. These conditions are generally considered to be unsuitable for both inverse suspension polymerization systems and inverse emulsion polymerization systems.

Irregularly shaped resins prepared by the method of the present invention have an increased-surface area. This improves both the water absorption rate and gel-strength of the resin. Additionally, in this polymerizing system the viscosity of the resin is suddenly increased by developing the Trommsdorff effect to conduct phase-transition.

It is possible to explain this phenomenon, as follows:

(1) one by first occurring phase-transition from a system having greater mechanical force by agitation than viscous force to another system wherein mechanical force and viscous force are balanced, and followed by phase-transition to the system having greater mechanical force by agitation than viscous force again.

(2) one by first occurring phase-transition from a system (namely W/O system) wherein main phase is hydrophobic, to a water and oil equilibrium phase system, and followed by phase-transition to the hydrophobic system (W/O system) again.

As a result of this phase-transition effect the water absorptive capacity is further improved due to chemical self-crosslinking in particles during polymerization, and physical pseudo-crosslinking by trapped entanglement of the main chain. Moreover, as a result of raising the polymerization temperature successively as mentioned above, the shape of polymer is not spherical but irregular.

In this preferred embodiment, the alkali metal acrylate, the hydrocarbon solvent, the water soluble radical polymerization initiator and the surface-crosslinking agent are the same as described in the foregoing first preferred embodiment and the crosslinking agent is preferably 0.005~15% by weight based on the polymer.

The process for preparation of the highly water absorptive resin according to the seventh preferred embodiment of the present invention is described in detail as follows:

(1) Preparation of the partially neutralized alkali metal acrylate

A reactor, equipped with a condenser, a dropping funnel and a stirrer, is charged with acrylic acid. An alkali metal hydroxide is dissolved in water in a beaker to form an alkali metal hydroxide solution. The alkali metal hydroxide solution is fed dropwise to the reactor through the dropping funnel while the mixture is kept below 30° C. The acrylic acid is neutralized, 50-100% by mole, to produce an equivalent amount of an alkali metal acrylate having the degree of neutralization of 50~100% by mole. When the neutralization step is conducted at a temperature of over 45° C., one of the reactants could be polymerized.

(2) Inverse suspension polymerization step

A reactor, with the condenser having a Dean-Stark trap, a pressure-equalizing dropping funnel and a stirrer is charged with a surfactant and a hydrocarbon solvent, and then the temperature of the reactor is raised to 70°~80° C. A mixture of the partially neutralized alkali metal acrylate prepared in step (1) and a water soluble radical polymerization initiator are slowly added to the reactor. The temperature is raised to 70° C., then reduced to 60°~67° C., and raised again to 70° C., and then to 75° C. Clots of gel in irregular shapes are obtained due to phase-transition.

(3) Azeotropic distilling step

The resultant polymer contains a large amount of water so that it is difficult for the crosslinking agent to react at the polymer surface. The moisture contained in the polymer is separated by azeotropic distillation to reduce the water content of the polymer to about 15 to 55% by weight. When the water content is less than 15% weight, it is uneconomic. On the other hand, when the water content is over 55% by weight, the effect of surface-crosslinking is decreased.

After separating the water from the polymer, the internal temperature of the reactor is maintained at room temperature. The solvent is then removed by filtration to obtain the polymer.

(4) Surface-crosslinking step

The polymer produced in step (3) is crosslinked using the crosslinking agent so as to improve the water absorption rate and gel-strength. A reactor equipped with a condenser, a stirrer, and a dropping funnel is charged with a polymer having a water content of 15~55% by weight and the solution of the crosslinking agent and methanol. The surface-crosslinking reaction is carried out at a temperature of 75° to 80° C. for 1 to 2 hours. The polymer thus treated is cooled to room temperature and the methanol is removed by filtration.

(5) Washing and drying step

To remove residual monomers, the obtained polymer is washed twice with methanol and filtered. The filtered polymer is dried at a temperature of 90° to 175° C. and passed through a 40-mesh wire gauze to obtain the water absorptive resin in particles having a uniform size. The water absorption rate and the water absorptive capacity of the obtained resin is measured by the filtering method.

The present invention is described in detail by the following examples, but it should be noted that the invention is not limited by these examples.

The term "the water absorptive capacity" used in the present invention means a value determined according to the following procedure: To 2,000 g of deionized water is added 1 g of the dried water absorptive resin. Water is absorbed by the polymer for 30 minutes, after which the polymer is collected by filtration with a 80-mesh metallic wire gauze. The volume of the swollen polymer obtained is measured, and the value is taken as the deionized water absorption capacity.

The saline solution-absorption rate is a value (g/g) calculated from the weight of the saline solution (0.9% by weight aqueous sodium chloride solution) which is absorbed by the polymer for 1, 3 and 5 minutes, respectively.

EXAMPLE 1

A one liter four-necked round-bottomed flask, equipped with a stirrer, a condenser having a Dean-Stark trap, a pressure equalizing dropping funnel and a nitrogen gas inlet pipe, was charged with 200 g of cyclohexane and 2.0 g of Ryoto Sugar Ester S-970® (manufactured by Mitsubishi-Kasei Food corporation). Nitrogen gas was introduced into the flask, so as to remove oxygen from the flask, and then the flask was heated to 85° C.

Separately, another one liter four-necked round-bottomed flask, equipped with a stirrer, a condenser and a dropping funnel was charged with 36 g of acrylic acid. The flask was cooled to room temperature, and a solution prepared by dissolving 15 g of sodium hydroxide in 50 g of distilled water was slowly added dropwise, resulting in an aqueous solution of 75% neutralized sodium acrylate.

Potassium persulfate (0.32 g) was dissolved thoroughly in 3.88 g of distilled water and added to the previously prepared sodium acrylate solution with stirring. This mixture was added dropwise to the flask containing cyclohexane and the surfactant using the pressure equalizing dropping funnel over 20 minutes. The reaction mixture was held at 85° C. for 1 hour to conduct the polymerization. At the completion of the polymerization, 28 g of water was removed from the produced polymer by azeotropic distillation, reducing the water content to 40% by weight.

The mixture was cooled to room temperature, the cyclohexane was removed by filtration, and the resulting polymer was transferred to a flask equipped with a condenser, a stirrer and a dropping funnel. Glycerol polyglycidyl ether (Epok 812, 0.375 g) was dissolved in 200 g of methanol, and the resulting solution was added via dropping funnel to the flask containing produced polymer. The resulting mixture was heated to 80° C., and maintained at that temperature for 1 hour. The flask was then cooled to reduce the inside temperature of the flask to room temperature, and the solvent was removed by filtration. The resulting polymer was washed twice with 40 g of methanol, filtered, and dried at 120° C. The dried polymer was passed through a 20-mesh wire gauze to obtain a highly water absorptive resin in particles having a uniform size.

The results are shown in Table 1.

EXAMPLE 2

A water absorptive resin was prepared in the same manner as described in Example 1 except that 0.25 g of Epok 812 was used as the crosslinking agent.

The results are shown in Table 1.

EXAMPLE 3

A water absorptive resin was prepared in the same manner as described in Example 1 except that 0.425 g of Epok 812 was used as the crosslinking agent.

The results are shown in Table 1.

EXAMPLE 4

A water absorptive resin was prepared in the same manner as described in Example 1 except that 0.625 g of Epok 812 was used as the crosslinking agent.

The results are shown in Table 1.

COMPARATIVE EXAMPLE 1

A water absorptive resin was prepared in the same manner as described in Example 1 except that the polymer was directly dried without removing the water.

The results are shown in Table 1.

COMPARATIVE EXAMPLE 2

A water absorptive resin was prepared in the same manner as described in Example 1 except that 28 g of water was separated from the polymer to reduce the water content to 40% by weight, prior to the drying step.

The results are shown in Table 1.

COMPARATIVE EXAMPLE 3

A water absorptive resin was prepared in the same manner as described in Example 1 except that the crosslinking agent was not used in the surface-crosslinking step.

The results are shown in Table 1.

TABLE 1

| | Absorption rate in a 0.9% NaCl aqueous solution (g/g polymer) | | | Absorptive capacity after 30 minutes (g/g polymer) | | gel-strength* |
|---|---|---|---|---|---|---|
| | 1 min. | 3 min. | 5 min. | In a 0.9% NaCl aqueous solution | In distilled water | |
| Example 1 | 83 | 95 | 95 | 98 | 1124 | o |
| Example 2 | 79 | 84 | 85 | 95 | 1096 | o |
| Example 3 | 80 | 88 | 90 | 98 | 1102 | o |
| Example 4 | 82 | 92 | 93 | 99 | 1115 | o |
| Comparative 1 | 13 | 25 | 29 | 47 | 512 | x |
| Comparative 2 | 21 | 27 | 35 | 52 | 553 | |
| Comparative 3 | 26 | 32 | 39 | 58 | 611 | |

<Note>
*o: Excellent : Normal x: Poor

EXAMPLE 5

A one liter four-necked round-bottomed flask, equipped with a stirrer, a condenser having a Dean-Stark trap, a pressure equalizing dropping funnel and a nitrogen gas inlet pipe, was charged with 150 g of cyclohexane and 2.0 g of Ryoto Sugar Ester S-970®. Nitrogen gas was introduced into the flask to remove oxygen from the flask, and the flask was then heated to 60° C.

Separately, another one liter four-necked round-bottomed flask, equipped with a stirrer, a condenser and a dropping funnel, was charged with 36 g of acrylic acid. While cooling the flask to room temperature, a solution prepared by dissolving 15 g of sodium hydroxide in 50 g of distilled water was added dropwise to produce an aqueous solution of 75% neutralized sodium acrylate.

Potassium persulfate (0.32 g) was dissolved thoroughly in 3.88 g of distilled water, added to the previously prepared sodium acrylate solution and stirred. The mixture was slowly added to the flask containing cyclohexane and the surfactant using the pressure equalizing dropping funnel over 1 hour. The mixture was held at 60° C. for 3 hours to conduct the polymerization. At the completion of the polymerization, 28 g of water was separated from the produced polymer by azeotropic distillation to reduce the water content to 40% by weight.

Epok 812 (0.2 g) was dissolved in 10 g of methanol and added to the polymer through the pressure equalizing dropping funnel. The reaction was allowed to proceed for 1 hour. After the mixture was cooled to room temperature, the solvent was removed to obtain the polymer. Methanol (350 g) and sulfuric acid (1.25 g) were combined and stirred. The polymer was added and the mixture was stirred to coagulate. After coagulation, methanol was removed by filtration. The product obtained was dried at 120° C. for 1 hour, and passed through a 20-mesh wire gauze to obtain a water absorptive resin in particles having a uniform size.

The results are shown in Table 2.

EXAMPLE 6

A water absorptive resin was prepared in the same manner as described in Example 5 except that 2.0 g of sulfuric acid was used in the coagulation step.

The results are shown in Table 2.

EXAMPLE 7

A water absorptive resin was prepared in the same manner as described in Example 5 except that 200 g of methanol was used in the coagulation step.

The results are shown in Table 2.

EXAMPLE 8

A water absorptive resin was prepared in the same manner as described in Example 5 except that 0.3 g of Epok 812 was used as the crosslinking agent.

The results are shown in Table 2.

COMPARATIVE EXAMPLE 4

A water absorptive resin was prepared in the same method as described in Example 5 except that 28 g of water was first separated from the polymer to reduce the water content to 40% by weight, prior to the drying step.

The results are shown in Table 2.

COMPARATIVE EXAMPLE 5

A water absorptive resin was prepared in the same method as described in Example 5 except that sulfuric acid was not used in the coagulation step.

The results are shown in Table 2.

COMPARATIVE EXAMPLE 6

A water absorptive resin was prepared in the same method as described in Example 5 except that Epok 812 was not used.

The results are shown in Table 2.

TABLE 2

| | Absorption rate in a 0.9% NaCl aqueous solution (g/g polymer) | | |
|---|---|---|---|
| | 1 min. | 3 min. | 5 min. |
| Example 5 | 53 | 55 | 52 |
| Example 6 | 51 | 53 | 51 |
| Example 7 | 49 | 52 | 52 |
| Example 8 | 53 | 54 | 54 |
| Comparative 4 | 21 | 35 | 41 |
| Comparative 5 | 34 | 41 | 31 |
| Comparative 6 | 14 | 31 | 38 |

EXAMPLES 9~12

A 500 mL four-necked round-bottomed flask, equipped with a stirrer, a condenser having a Dean-Stark equipment, a dropping funnel and a nitrogen gas inlet pipe, was charged with 200 Ml of n-hexane and 1.5 g of sorbitan monostearate, and the flask was heated to 65° C. Separately, another flask was charged with 30 g of acrylic acid and the acid was neutralized with a solution prepared by dissolving 13.4 g of sodium hydroxide in 39 g of water. The concentration of the aqueous monomer in the solution was 45% and the amount of water contained was 55%. Potassium persulfate (0.1 g)

was dissolved therein, and the solution was fed dropwise via dropping funnel over 30 minutes to the reaction flask containing the n-hexane solution. Nitrogen gas was introduced into the flask during the polymerization. Water was removed from the polymer obtained by azeotropic distillation, reducing the water content to 20%, 30%, 40% and 50% respectively. To each of the resulting solutions was added an aqueous solution prepared by dissolving 0.08 g of polyglycerol polyglycidyl ether in 1 Ml of water, and stirring was continued at 70° C. for 3 hours. At the completion of the polymerization, n-hexane was removed from the polymer. The polymer was coagulated by addition of 200 g of methanol and 0.2 g of sulfuric acid.

After coagulation, the methanol was removed, and the polymer was dried under vacuum at 80° C. to obtain a highly water absorptive resin.

EXAMPLE 13

A highly water absorptive resin was prepared in the same manner as described in Example 9 except as follows:

Ethyl cellulose T-50 (1.5 g, manufactured by Hercules Incorporated) was used instead of sorbitan monostearate. After the polymerization, the content of water was reduced to 40% by azeotropic distillation. Polyglycerol polyglycidyl ether (0.1 g, dissolved in 1 Ml of water) was added to the reaction flask, and stirring was continued for 2 hours at 70° C. At the completion of the reaction, n-hexane was removed from the polymer, and 230 g of methanol and 0.5 g of sulfuric acid were added to the polymer to effect coagulation.

EXAMPLE 14

A highly water absorptive resin was prepared in the same manner as described in Example 13 except as follows:

The concentration of aqueous monomer was 35%. After the polymerization, polyglycerol polyglycidyl ether (0.15 g, dissolved in 1 Ml of water) was added to the reaction flask and stirred for 3 hours at 75° C. n-Hexane was removed from the polymer, and 250 g of methanol and 0.4 g of sulfuric acid were added to the polymer to effect coagulation.

COMPARATIVE EXAMPLES 7~10

Comparative samples were prepared in the same manner as described in Example 9 except as follows:

The content of water was reduced to 10% (Comparative Example 7), 15% (Comparative Example 8), 55% (Comparative Example 9) and 60% (Comparative Example 10) by weight, respectively. After the polymerization, 0.1 g of polyglycerol polyglycidyl ether dissolved in 1 Ml of water was added to the reaction flask, and stirred for 2 hours at 70° C. n-Hexane was removed from the polymer, and 200 g of methanol and 0.4 g of sulfuric acid were added to the polymer to effect coagulation.

COMPARATIVE EXAMPLE 11

Comparative sample 11 was prepared in the same manner as described in Example 9 except as follows:

The content of water was reduced to 30% by weight. Polyglycerol polyglycidyl ether (0.1 g) dissolved in 1 Ml of water was added to the reaction flask, and stirred for 3 hours at 70° C.

COMPARATIVE EXAMPLE 12

Comparative sample 12 was prepared in the same manner as described in Example 13 except as follows:

The concentration of the aqueous monomer was 35%, and the content of water after polymerization was 40% by weight. Polyglycerol polyglycidyl ether (0.1 g, dissolved in 1 mL of water) was added to the reaction flask, and stirred for 3 hours at 75° C.

The absorption characteristics of the highly water absorptive resins obtained in Examples 9~14 and the comparative samples obtained in Comparative Examples 7~12 are shown in Table 3. Table 3 illustrates that the polymer of the present invention has excellent resistance to salts, and a high absorption rate in saline solution.

TABLE 3

| | Absorption rate in saline solution (g/g) | | | Absorptive capacity in |
|---|---|---|---|---|
| | 1 min. | 3 min. | 5 min. | deionized water (g/g) |
| Example 9 | 60 | 62 | 62 | 950 |
| Example 10 | 59 | 60 | 62 | 920 |
| Example 11 | 61 | 62 | 63 | 940 |
| Example 12 | 63 | 63 | 63 | 950 |
| Example 13 | 60 | 60 | 61 | 930 |
| Example 14 | 57 | 57 | 57 | 920 |
| Comparative 7 | 40 | 42 | 42 | 850 |
| Comparative 8 | 38 | 38 | 37 | 800 |
| Comparative 9 | 41 | 41 | 41 | 920 |
| Comparative 10 | 39 | 41 | 44 | 920 |
| Comparative 11 | 25 | 27 | 29 | 530 |
| Comparative 12 | 28 | 30 | 31 | 510 |

EXAMPLES 15~17

A 500 mL four-necked round-bottomed flask, equipped with a stirrer, a condenser having a Dean-Stark trap, dropping funnel and a nitrogen gas inlet pipe, was charged with 200 mL of n-hexane and 15 g of sorbitan monostearate, and the flask was heated to 65° C. In another flask, 30 g of acrylic acid was neutralized with a solution prepared by dissolving 13.4 g of sodium hydroxide in 39 g of water. The concentration of the aqueous monomer in the solution was 45% by weight and the amount of water contained was 55% by weight. Potassium persulfate (0.1 g) was added, and the resulting solution was added via dropping funnel to the reaction flask containing the n-hexane solution over about 30 minutes.

Nitrogen gas was introduced to the reaction flask during polymerization, and the resulting solution was kept at 65° C. for 2 hours to complete the polymerization. Ethylene glycol diglycidyl ether (0.08 g, dissolved in 1 mL of water) was added to the reaction flask and the mixture was kept at 70° C. for 2 hours. After the reaction was complete, n-hexane was removed. The obtained polymer was added to beakers containing, respectively, 200 g/0.2 g, 200 g/0.5 g and 200 g/1.0 g of methanol and sulfuric acid to coagulate the polymer. After coagulation, the methanol was removed, and the resulting polymer was dried under vacuum at 80° C. to obtain a highly water absorptive resin.

EXAMPLE 18

A water absorptive resin was prepared in the same manner as described in Example 15 except that 1.0 g of ethyl cellulose T-50 was used instead of sorbitan monostearate.

After polymerization was complete, 0.05 g of glycerol diglycidyl ether dissolved in 1 mL of water was added to the reaction flask, and the mixture was stirred for 2 hours at 70° C. n-Hexane was removed, and the polymer obtained was added to a beaker containing 250 g of methanol and 0.4 g of sulfuric acid to coagulate the polymer. Methanol was removed, and the resulting polymer was dried in a vacuum oven at 80° C. to obtain a highly water absorptive resin.

EXAMPLE 19

A water absorptive resin was prepared in the same manner as described in Example 18 except that the concentration of monomer in the aqueous monomer solution was adjusted to 35%. After polymerization, 0.2 g of polyethylene glycol diglycidyl ether (n=9) dissolved in 1 mL of water was added to the reaction flask and the mixture was stirred for 3 hours at 75° C. n-Hexane was removed, and the polymer was added to a beaker containing 230 g of methanol and 0.5 g of sulfuric acid to coagulate the polymer. Methanol was removed, and the resulting polymer was dried in a vacuum oven at 80° C. to obtain a highly water absorptive resin.

EXAMPLE 20

A water absorptive resin was prepared in the same manner as described in Example 18 except that 1.2 g of ethyl cellulose N-100 (manufactured by Hercules Incorporated) was used instead of ethyl cellulose T-50. After polymerization, 0.09 g of ethylene glycol diglycidyl ether dissolved in 1 mL of water was added to the reaction flask, and the mixture was stirred for 2 hours at 70° C. n-Hexane was removed, and the polymer was added to a beaker containing 200 g of methanol and 1.0 g of sulfuric acid to coagulate the polymer. Methanol was removed, and the resulting polymer was dried in a vacuum oven at 80° C. to obtain a highly water absorptive resin.

COMPARATIVE EXAMPLES 13~16

Water absorptive resins were prepared in the same manner as described in Example 15 except as follows:

After polymerization, 0.08 g of ethylene glycol diglycidyl ether dissolved in 1 mL of water was added to the reaction flask, and the concentration of monomer was adjusted to 35%. After polymerization, 0.3 g of polyethylene glycol diglycidyl ether (n=9) dissolved in 1 mL of water was added to the reaction flask, and the mixture was stirred for 3 hours at 75° C.

COMPARATIVE EXAMPLE 17

A water absorptive resin was prepared in the same manner as described in Example 20 except that 0.01 g of ethylene glycol diglycidyl ether dissolved in 1 mL of water was added to the reaction flask, and the mixture was stirred for 2 hours at 75° C.

The absorption characteristics of the highly water absorptive resins obtained in Examples 15~20 and the samples obtained in Comparative Examples 13~17 are shown in Table 4.

Table 4 illustrates that the polymer of the present invention has excellent resistance to salts and the high absorption rate in saline solution.

TABLE 4

| | Absorption rate in saline solution (g/g) | | | Absorptive capacity in |
|---|---|---|---|---|
| | 1 min. | 3 min. | 5 min. | deionized water (g/g) |
| Example 15 | 40 | 43 | 43 | 850 |
| Example 16 | 42 | 42 | 43 | 900 |
| Example 17 | 41 | 43 | 45 | 930 |
| Example 18 | 41 | 41 | 42 | 900 |
| Example 19 | 38 | 38 | 40 | 890 |
| Example 20 | 43 | 43 | 44 | 950 |
| Comparative 13 | 21 | 23 | 27 | 510 |
| Comparative 14 | 23 | 23 | 23 | 540 |
| Comparative 15 | 20 | 24 | 24 | 530 |
| Comparative 16 | 18 | 20 | 25 | 500 |
| Comparative 17 | 22 | 25 | 27 | 530 |

EXAMPLE 21

A four-necked round-bottomed flask, equipped with a stirrer, a condenser having a Dean-Stark trap, a dropping funnel and a nitrogen gas inlet pipe, was charged with 160 g of cyclohexane and 2.4 g of Ryoto Sugar Ester S-970® (HLB=9), and the flask was heated to 60° C. A solution of aqueous sodium acrylate (45% by weight, 75% neutralized, 80 g) was mixed with an aqueous solution of 2 g of 2-acrylamido-2-methyl-1-propanesulfonic acid (which was neutralized with 0.44 g of sodium hydroxide) and 0.1 g of potassium persulfate. The resulting solution was added dropwise to the reaction flask. Polymerization was held for about 2 hours at 70° C.

The water was separated from the produced polymer to reduce the water content to 40% by weight. Epok 812® (0.12 g) was dissolved in a little methanol and was added to the polymer and refluxed for 1 hour.

The polymer obtained was filtered and again dissolved in methanol. A little sulfuric acid was added to coagulate the polymer. The coagulated polymer was filtered again, dried, and passed through a 20-mesh wire gauze to obtain a highly water absorptive resin in particles having a uniform size.

EXAMPLE 22

A water absorptive resin was prepared in the same manner as described in Example 21 except that only 0.22 g of sodium hydroxide was used to neutralize 2 g of 2-acrylamido-2-methyl-1-propane sulfonic acid.

EXAMPLE 23

A water absorptive resin was prepared in the same manner as described in Example 21 except that 0.66 g of sodium hydroxide was used to neutralize 3 g of 2-acrylamido-2-methyl-1-propane sulfonic acid.

COMPARATIVE EXAMPLE 18

A water absorptive resin was prepared in the same manner as described in Example 21 except that 2-acrylamido-2-methyl-1-propane sulfonic acid was not used.

COMPARATIVE EXAMPLE 19

A water absorptive resin was prepared in the same manner as described in Example 21 except that the polymer was not coagulated by sulfuric acid.

COMPARATIVE EXAMPLE 20

A water absorptive resin was prepared in the same manner as described in Example 21 except that 2-acrylamido-2-methyl-1-propane sulfonic acid was not used and the polymer was not coagulated by sulfuric acid.

The absorptive capacities (in a 0.9% sodium chloride aqueous solution for 1 minute) of the water absorptive resins prepared in Examples 21∼23 and Comparative Examples 18∼20 are shown in Table 5.

TABLE 5

| Example 21 | Example 22 | Example 23 | Comparative 18 | Comparative 19 | Comparative 20 |
|---|---|---|---|---|---|
| 62 | 65 | 63 | 45 | 50 | 35 |

(g/g polymer)

EXAMPLE 24

A four-necked round-bottomed flask, equipped with a stirrer, a condenser having a Dean-Stark trap, a dropping funnel and a nitrogen gas inlet pipe, was charged with 160 g of n-hexane and 1.4 g of Ryoto Sugar Ester S-370F® (HLB value=3), and the flask was heated to 50° C.

An aqueous sodium acrylate solution (45% by weight, 75% neutralized, 80 g) was mixed with an aqueous solution prepared from 2 g of 2-acrylamido-2-methyl-1-propane sulfonic acid which was neutralized with 0.44 g of sodium hydroxide and an aqueous solution of 0.1 g of potassium persulfate. The resulting solution was added dropwise to the reaction mixture. Polymerization was conducted for about 2 hours.

Water was separated from the produced polymer to reduce the water content to 40% by weight. EPOK 812® (0.12 g) was dissolved in a little methanol and was added to the reaction mixture. The solution was refluxed for 1 hour and the polymer obtained was filtered, dissolved in methanol, and coagulated by the addition of sulfuric acid. The coagulated product was filtered, dried, and passed through a 20-mesh wire gauze to obtain a water absorptive resin.

EXAMPLE 25

A water absorptive resin was prepared in the same manner as described in Example 24 except that only 0.22 g of sodium hydroxide was used to neutralize 2 g of 2-acrylamido-2-methyl-1-propane sulfonic acid.

EXAMPLE 26

A water absorptive resin was prepared in the same manner as described in Example 24 except that 0.66 g of sodium hydroxide was used to neutralize 3 g of 2-acrylamido-2-methyl-1-propane sulfonic acid.

COMPARATIVE EXAMPLE 21

A water absorptive resin was prepared in the same manner as described in Example 24 except that 2-acrylamido-2-methyl-1-propane sulfonic acid was not used.

COMPARATIVE EXAMPLE 22

A comparative sample was prepared in the same manner as described in Example 24 except that the polymer was not coagulated by sulfuric acid.

COMPARATIVE EXAMPLE 23

A comparative sample was prepared in the same manner as described in Example 24 except that 2-acrylamido-2-methyl-1-propane sulfonic acid was not used and the polymer was not coagulated by sulfuric acid.

The absorptive capacities (in a 0.9% sodium chloride aqueous solution for 1 minute) of the resins prepared in Examples 24∼26 and Comparative Examples 21∼23 are shown in Table 6.

TABLE 6

| Example 24 | Example 25 | Example 26 | Comparative 21 | Comparative 22 | Comparative 23 |
|---|---|---|---|---|---|
| 50 | 55 | 52 | 30 | 40 | 25 |

(g/g polymer)

EXAMPLE 27

A one liter four-necked round-bottomed flask, equipped with a stirrer, a condenser having a Dean-Stark trap, a pressure equalizing dropping funnel and a nitrogen gas inlet pipe, was charged with 200 g of cyclohexane and 2.0 g of Ryoto Sugar Ester S-970®.

Nitrogen gas was introduced into the flask to remove oxygen from the flask, and then the flask was heated to 75° C. in an oil bath.

Another one liter four-necked round-bottomed flask, equipped with a stirrer, a condenser and a dropping funnel, was charged with 36 g of acrylic acid.

While cooling to room temperature, the acid was 75% neutralized by the dropwise addition of a solution, prepared by dissolving 15 g of sodium hydroxide in 50 g of distilled water.

Potassium persulfate (0.12 g) was dissolved thoroughly in 3.88 g of distilled water, and this solution was mixed with the previously prepared sodium acrylate solution and stirred. The mixture was added rapidly to the flask containing cyclohexane and the surfactant through the pressure equalizing dropping funnel over about 10 minutes.

The internal temperature of the flask was cycled from 70° C., to 64° C., to 70° C. again, and to 75° C. (the temperature of the oil bath was as follows: 85° C.→73° C.→85° C.→88° C.), to undergo phase-transition. Thereafter, the temperature of the oil bath was held to 90° C. for 1 hour to complete the polymerization. Water (28 g) was separated from the produced polymer by azeotropic distillation to reduce the water content to 40% by weight. After cooling the flask to room temperature, cyclohexane was filtered off, and the polymer was introduced to a flask equipped with a condenser, stirrer and dropping funnel.

Epok 812 (0.375 g) and 200 g of methanol were combined and added via dropping funnel to the flask containing the polymer. The temperature was held at 80° C. for 1 hour.

Thereafter, the flask was cooled to room temperature, and the solution was filtered to obtain the polymer.

The polymer obtained was washed with 40 g of methanol, filtered, and dried to obtain a water absorptive resin having an irregular shape. This resin was passed through a 20-mesh wire gauze to obtain a water absorptive resin in particles having a uniform size.

The results are shown in Table 7. The microphotograph of Example 27 is shown in FIG. 1.

EXAMPLE 28

A water absorptive resin was produced in the same manner as described in Example 27 except that 0.25 g of Epok 812 was used.

The results are shown in Table 7.

EXAMPLE 29

A water absorptive resin was produced in the same manner as described in Example 27 except that 0.425 g of Epok 812 was used.

The results are shown in Table 7.

EXAMPLE 30

A water absorptive resin was produced in the same manner as described in Example 27 except that 0.625 g of Epok 812 was used.

The results are shown in Table 7.

EXAMPLE 31

A water absorptive resin was produced in the same manner as described in Example 27 except that 36 g of acrylic acid was neutralized to 70% by adding 14 g of sodium hydroxide in 47.1 g of distilled water in the polymerization step.

The results are shown in Table 7.

EXAMPLE 32

A water absorptive resin was produced in the same manner as described in Example 27 except that 36 g of acrylic acid was neutralized to 65% by adding 13 g of sodium hydroxide in 46.9 g of distilled water in the polymerization step.

The results are shown in Table 7.

EXAMPLE 33

A water absorptive resin was produced in the same manner as described in Example 27 except that 36 g of acrylic acid was neutralized to 60% by adding 12 g of sodium hydroxide in 46.6 g of distilled water in the polymerization step.

The results are shown in Table 7.

COMPARATIVE EXAMPLE 24

A comparative sample was produced in the same manner as described in Example 27 except that 28 g of water was first separated from the polymer to reduce the water content to 40% by weight, followed by the drying step.

The results are shown in Table 7.

COMPARATIVE EXAMPLE 25

A comparative sample was produced in the same manner as described in Example 27 except that 28 g of water was first separated from the polymer to reduce the water content to 40% by weight, and the polymer was washed twice with 40 g of methanol, followed by the drying step.

The results are shown in Table 7.

COMPARATIVE EXAMPLE 26

A comparative sample was produced in the same manner as described in Example 27 except that the temperature of the oil bath was maintained at 65° C. during the polymerization step.

Figure 2:
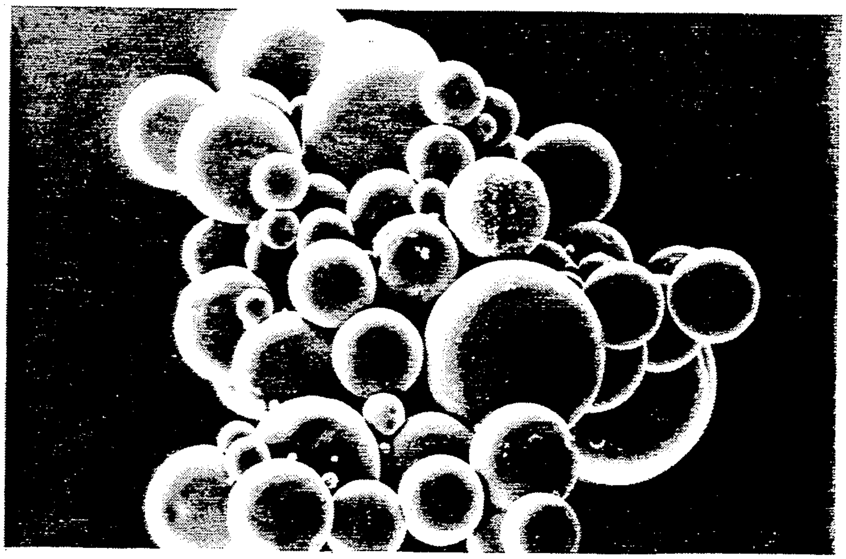

The results are shown in Table 7 and the microphotograph is shown in FIG. 2.

COMPARATIVE EXAMPLE 27

A comparative sample was produced in the same manner as described in Example 33 except that 28 g of water was first separated from the polymer to reduce the water content to 40% by weight, followed by the drying step.

The results are shown in Table 7.

TABLE 7

|  | Absorption rate in a 0.9 solution chloruide aqueous solution (g/g polymer) | | | Absorptive capacity after 30 minutes (g/g polymer) | | Gel-strength* | Shape of particle |
|---|---|---|---|---|---|---|---|
|  | 1 min. | 3 min. | 5 min. | In a 0.9% sod-sodium chloride aqueous solution | In distilled water | | |
| Example 27 | 74 | 88 | 92 | 94 | 1107 | o | irregular |
| Example 28 | 58 | 78 | 82 | 93 | 992 | o | irregular |
| Example 29 | 57 | 77 | 84 | 87 | 993 | o | irregular |
| Example 30 | 65 | 87 | 90 | 94 | 1108 | o | irregular |
| Example 31 | 67 | 80 | 84 | 87 | 911 | o | irregular |
| Example 32 | 63 | 82 | 90 | 100 | 1402 |  | irregular |
| Example 33 | 73 | 105 | 118 | 148 | 1946 |  | irregular |
| Comparative 24 | 30 | 66 | 76 | 82 | 840 | x | irregular |
| Comparative 25 | 30 | 67 | 79 | 93 | 851 | x | irregular |
| Comparative 26 | 42 | 57 | 61 | 68 | 620 |  | spherical |
| Comparative 27 | 28 | 42 | 58 | 98 | 970 | x | spherical |

<Note>
*o: excellent   : normal x: poor

What is claimed is:

1. A process for producing a highly water absorptive amorphous resin, which comprises
   (a) suspending an aqueous solution of partially neutralized alkali metal acrylate wherein about 50 to 100% by mole of the carboxyl group has been neutralized to its alkali metal salt and at least one water soluble radical polymerization initiator, in a hydrocarbon solvent containing a surfactant having a HLB value of 8~12;
   (b) subjecting the mixture to inverse suspension polymerization while raising the internal temperature of the reactor successively to 70° C., to 60°~67° C., and then to 75° C., to undergo phase-transition;
   (c) during or after the polymerization, separating the moisture from the produced polymer by azeotropic distillation to reduce the water content to about 15 to 55% by weight, and filtering to remove the solvent;
   (d) adding a crosslinking agent having three or more reactive epoxy groups which is dissolved in methanol, wherein the amount of the crosslinking agent is 0.005~15% by weight based on the produced polymer, and incubating for 1~2 hours at temperatures 70° to 85° C.; and
   (e) washing with methanol, filtering, and drying at temperatures of 90° to 175° C. to obtain the water absorptive resin.

2. The process according to claim 1, wherein the surfactant is sorbitan monolaurate or Ryoto Sugar Ester S-970®.

3. The according to claim 1, wherein the hydrocarbon solvent is selected from the group consisting of n-hexane, n-heptane and cyclohexane.

4. The process according to claim 1, wherein the hydrocarbon solvent is cyclohexane.

5. The process according to claim 1, wherein the water soluble radical polymerization initiator is selected from the group consisting of ammonium persulfate, potassium persulfate and hydrogen peroxide.

6. The process according to claim 1, wherein the water soluble radical polymerization initiator is potassium persulfate.

7. The process according to claim 1, wherein the crosslinking agent is selected from the group consisting of glycerol polyglycidyl ether, trimethylol propane polyglycidyl ether and sorbitol polyglycidyl ether.

8. The process according to claim 1, wherein the partially neutralized alkali metal acrylate is prepared by addition of an alkali metal hydroxide such as sodium hydroxide, lithium hydroxide or potassium hydroxide.

* * * * *